US00PP28216P3

(12) United States Plant Patent
Mehlenbacher et al.

(10) Patent No.: US PP28,216 P3
(45) Date of Patent: Jul. 25, 2017

(54) ***CORYLUS* PLANT NAMED 'BURGUNDY LACE'**

(50) Latin Name: ***Corylus avellana* cultivar**
Varietal Denomination: Burgundy Lace

(71) Applicant: Oregon State University, Corvallis, OR (US)

(72) Inventors: Shawn A. Mehlenbacher, Corvallis, OR (US); David C. Smith, Corvallis, OR (US); Rebecca L. McCluskey, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 134 days.

(21) Appl. No.: 14/756,596

(22) Filed: Sep. 21, 2015

(65) Prior Publication Data

US 2017/0086341 P1 Mar. 23, 2017

(51) Int. Cl.
*A01H 5/12* (2006.01)

(52) U.S. Cl.
USPC ..... Plt./152

(58) Field of Classification Search
USPC ..... Plt./152
See application file for complete search history.

(56) References Cited

PUBLICATIONS

Bassil et al, "Additional Microsatellite Markers of the European Hazelnut," *Acta Hortic.* vol. 686, pp. 105-110, 2005.
Bassil et al, "Microsatellite Markers in Hazelnut: Isolation, Characterization, and Cross-species Amplification," *J. Amer. Soc. Hort. Sci.,* vol. 130(4), pp. 543-549, 2005.
Bassil et al, "Nuclear and chloroplast microsatellite markers to assess genetic diversity and evolution in hazelnut species, hybrids and cultivars," *Genet. Resour. Crop Evol.,* vol. 60(2), pp. 543-568, 2012.
Boccacci et al, "Characterization and evaluation of microsatellite loci in European hazelnut (*Corylus avellana* L.) and their transferability to other *Corylus* species," *Molecular Ecology Notes,* vol. 5, pp. 934-937, 2005.
Boccacci et al, "DNA typing and genetic relations among European hazelnut (*Corylus avellana* L.) cultivars using microsatellite markers," *Genome,* vol. 49, pp. 598-611, 2006.
Gökirmak et al, "Characterization of European hazelnut (*Corylus avellana*) cultivars using SSR markers," *Genet. Resour. Crop Evol.,* vol. 56(2), pp. 147-172, 2008.
Gürcan et al, "Genetic diversity in hazelnut (*Corylus avellana* L.) cultivars from Black Sea countries assessed using SSR markers," *Plant Breeding,* vol. 129, pp. 422-434, 2010.
Gürcan et al, "Development, characterization, segregation, and mapping of microsatellite markers for European hazelnut (*Corylus avellana* L.) from enriched genomic libraries and usefulness in genetic diversity studies," *Tree Genetics & Genomes,* vol. 6, pp. 513-531, 2010.
Gürcan et al, "Transferability of Microsatellite Markers in the Betulaceae," *J. Amer. Soc. Hort. Sci.* 135(2), pp. 159-173, 2010.
Gürcan and Mehlenbacher. "Development of microsatellite marker loci for European hazelnut (*Corylus avellana* L.) from ISSR fragments," *Molecular Breeding* 26:551-559, 2010.
Mehlenbacher et al., "Inheritance of the Cutleaf Trait in Hazelnut," *HortScience,* vol. 30(3), pp. 611-612, 1995.
Mehlenbacher et al., "'Tonda Pacifica' hazelnut," *HortScience* 46:505-508, 2011.
Mehlenbacher et al., "'Santiam' hazelnut" *HortScience* 42:715-717, 2007.
Mehlenbacher et al., "RAPD markers linked to eastern filbert blight resistance in *Corylus avellana,*" *Theor. Appl. Genet.,* vol. 108, pp. 651-656, 2004.
Sathuvalli et al., "Characterization of American hazelnut (*Corylus americana*) accessions and *Corylus americana*×*Corylus avellana* hybrids using microsatellite markers," *Genet. Resour. Crop. Evol.,* vol. 59, pp. 1055-1075, 2012.

*Primary Examiner* — Anne Grunberg
(74) *Attorney, Agent, or Firm* — Klarquist Sparkman, LLP

(57) ABSTRACT

A new and distinct *Corylus* plant named 'Burgundy Lace' characterized by rich dark burgundy-colored developing leaves and burgundy-colored fully expanded leaves during the spring and summer; deeply dissected leaves; burgundy color of the catkins and leaf buds; moderate vigor and upright-spreading plant habit; resistance to eastern filbert blight (EFB) caused by the fungus *Anisogramma anomala* (Peck) E. Müller; presence of random amplified polymorphic DNA markers 152-800 and 258-580 in DNA; expression of incompatibility alleles $S_6$ and $S_{20}$ in the styles; catkins that are abnormal and small, and produce little pollen; and DNA fingerprints at 14 of 24 microsatellite marker loci differ from 'Cutleaf'.

9 Drawing Sheets

ACKNOWLEDGMENT OF GOVERNMENT SUPPORT

This invention was made with government support under Specific Cooperative Agreement No. 58-5358-4-025 awarded by the United States Department of Agriculture. The government has certain rights in the invention.

Botanical denomination: *Corylus avellana* cultivar.

Variety designation: 'Burgundy Lace'.

BACKGROUND

The present disclosure relates to a new and distinct cultivar of *Corylus* plant, botanically known as *Corylus avellana*, and hereinafter referred to by the name 'Burgundy Lace'.

The new *Corylus* resulted from a controlled cross of female parent OSU 562.034 (unpatented)×OSU 562.062 (unpatented) made in 1998 to create a new ornamental cultivar (FIG. 1). OSU 562.034 is from a cross of 'Cutleaf'×

VR6-28 (unpatented), and OSU 562.062 is from a cross of 'Cutleaf'×Redleaf #3 (unpatented). The grandparent 'Cutleaf '(unpatented) is known as *Corylus avellana* f. *heterophylla*, for which the form names laciniata, urticifolia, quercifolia and incisa pinnatifida are also used. VR6-28 is from a cross of 'Riccia di Talanico'×'Gasaway', and carries a dominant allele for a very high level of resistance to eastern filbert blight (EFB) from 'Gasaway' (unpatented). OSU 562.062 and Redleaf #3 carry a dominant allele for leaf anthocyanin. Redleaf #3 is an open-pollinated seedling of 'Barcelona' (unpatented). The pollen parent is believed to be the Redleaf 'Rode Zeller' (syn. 'Rote Zellernuss') (unpatented).

Hybrid seeds from the controlled cross were harvested in August 1998, stratified, and the resulting seedlings grown in a glasshouse during the summer of 1999. Seedlings that combined red leaf color and the 'Cutleaf' trait were preferred, and 38 of the 40 seedlings planted in the field in October 1999 combined these two traits. 'Burgundy Lace' was discovered and selected as a single plant within the progeny of the stated cross-pollination in a controlled environment in Corvallis, Oreg., USA. The new variety was originally assigned the designation OSU 954.076, which indicates the row and tree location of the original seedling.

The new cultivar was asexually reproduced by rooted suckers annually for five years (2005, 2006, 2008, 2011 and 2013) in Corvallis, Oreg. The unique features of this new *Corylus* are stable and reproduced true-to-type in successive generations of asexual reproduction.

SUMMARY

The following traits have been observed and are determined to be the unique characteristics of 'Burgundy Lace'. These characteristics in combination distinguish 'Burgundy Lace' as a new and distinct cultivar:

1. Rich dark burgundy-colored developing leaves and burgundy-colored fully expanded leaves during the spring and summer.
2. Deeply dissected leaves.
3. Burgundy color of the catkins and leaf buds.
4. Moderate vigor and upright-spreading plant habit.
5. Resistance to eastern filbert blight (EFB) caused by the fungus *Anisogramma anomala* (Peck) E. Müller.
6. Presence of random amplified polymorphic DNA markers 152-800 and 268-580 in DNA of 'Burgundy Lace' amplified by the polymerase chain reaction. These two markers are linked to a dominant allele for resistance to eastern filbert blight from the cultivar 'Gasaway' (unpatented).
7. Expression of incompatibility alleles $S_6$ and $S_{20}$ in the styles.
8. Catkins that are abnormal and small, and produce little pollen.
9. DNA fingerprints of 'Burgundy Lace' differ from 'Cutleaf' at 14 of 24 microsatellite marker loci. Additional DNA fingerprints of 'Gasaway' and 'Rode Zeller', which are ancestors of 'Burgundy Lace', and 12 other reference cultivars, are shown in Table 7.

'Burgundy Lace' is well-suited to the ornamental market. 'Burgundy Lace' combines red leaf color, deeply dissected leaves, and resistance to eastern filbert blight (EFB) caused by *Anisogramma anomala* (Peck) E. Müller. Comparisons in two trials conducted in Corvallis, Oreg., plants of 'Burgundy Lace' in the guard rows differed from plants of the *Corylus avellana* cultivars 'Barcelona' (unpatented) and 'Jefferson' (unpatented), and other cultivars and selections of *Corylus avellana* known to the Inventors primarily in nut size, nut shape, kernel percentage (ratio of kernel weight to nut weight), frequency of defects (blank nuts, moldy kernels, twins, etc.), time of pollen shed, time of nut maturity, length of the husk or involucre, and plant size.

The tree is moderately vigorous, similar in size to 'Jefferson', and has a desirable upright-spreading growth habit that should be easy to manage in a landscape setting. The nuts are small and the kernels are edible, but nut yields are low and quality is not suitable for the kernel market. 'Burgundy Lace' has far fewer blanks (shells lacking kernels) than 'Cutleaf'. 'Burgundy Lace' has intermediate ratings for bud mite (primarily *Phytoptus avellanae* Nal.), similar to 'Clark'. Like its grandparent 'Cutleaf', catkins of 'Burgundy Lace' shed very little pollen. Pollen shed and female receptivity are late.

DNA markers and field observations indicate that 'Burgundy Lace' has resistance to eastern filbert blight (EFB) caused by the fungus *Anisogramma anomala* (Peck) E. Müller. The resistance is conferred by a dominant allele from 'Gasaway'. EFB is now present throughout the Willamette Valley and in the eastern USA where it naturally occurs on the wild American hazelnut (*C. americana*), but causes little damage. Pruning to remove cankers and fungicide applications are currently used to manage the disease in susceptible cultivars. Thus, 'Burgundy Lace' is suitable for planting in areas with high disease pressure.

BRIEF DESCRIPTION OF THE DRAWINGS

The accompanying colored photographs illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

FIG. 2 is a chart showing time of pollen shed (green), female receptivity (red) and leaf budbreak for 'Burgundy Lace' and 'Cutleaf' over two years for ornamental hazelnut selection.

FIG. 14 shows the lower surface of the leaves and nuts, and FIG. 15 shows the upper surface of the leaves and nuts.

DETAILED DESCRIPTION

Figure 1:
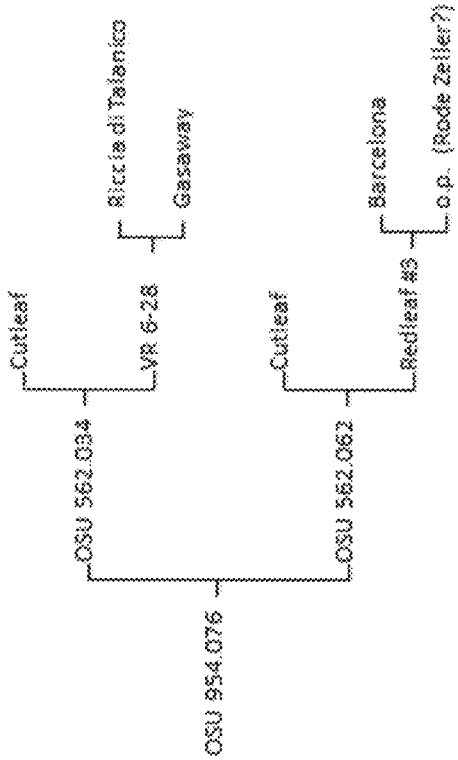
FIG. 1 is a chart showing the pedigree of hazelnut selection 'Burgundy Lace' (OSU 954.076).
Figure 4:
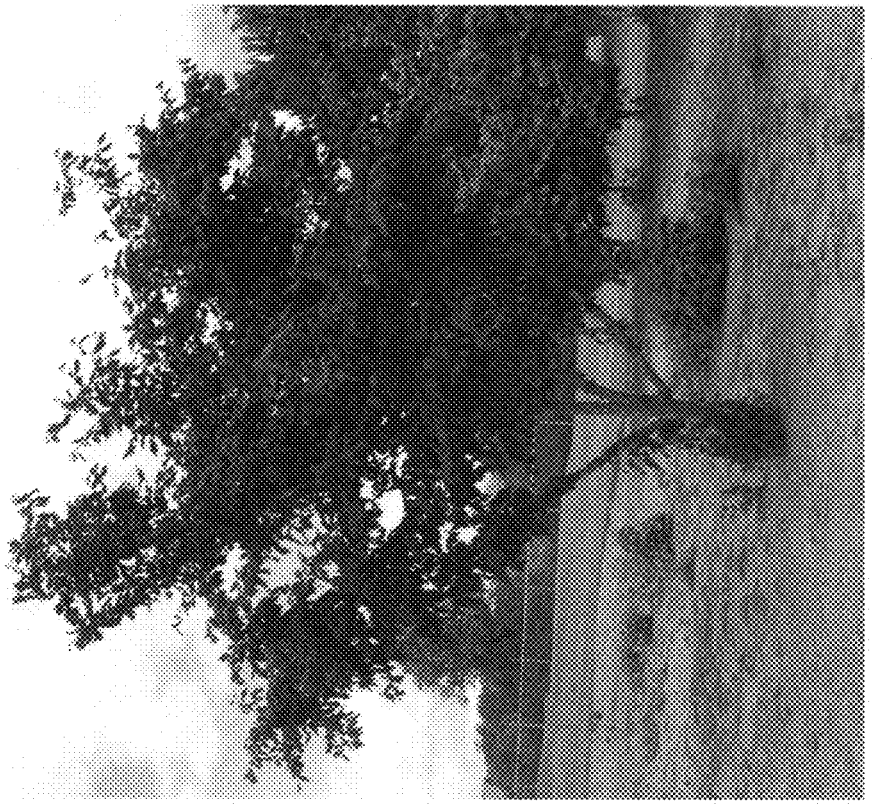
FIG. 4 is a digital image taken in June of the $5^{th}$ growing season of the original 'Burgundy Lace' tree growing in Corvallis, Oreg.
Figure 3:
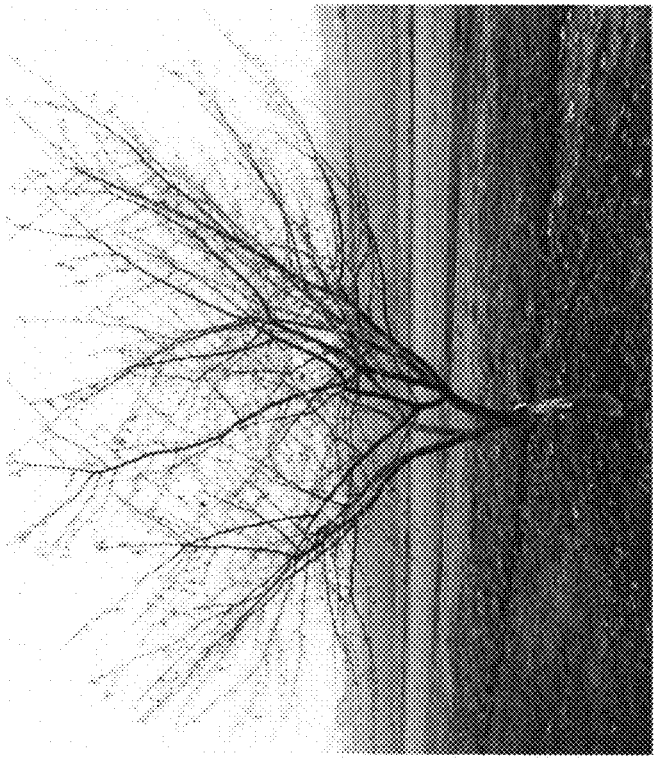
FIG. 3 is a digital image taken at end of the $6^{th}$ growing season of a tree of 'Burgundy Lace' growing in Corvallis, Oreg., in the winter, showing upright-spreading growth habit. Tree was planted in the spring of 2007.
Figure 6:
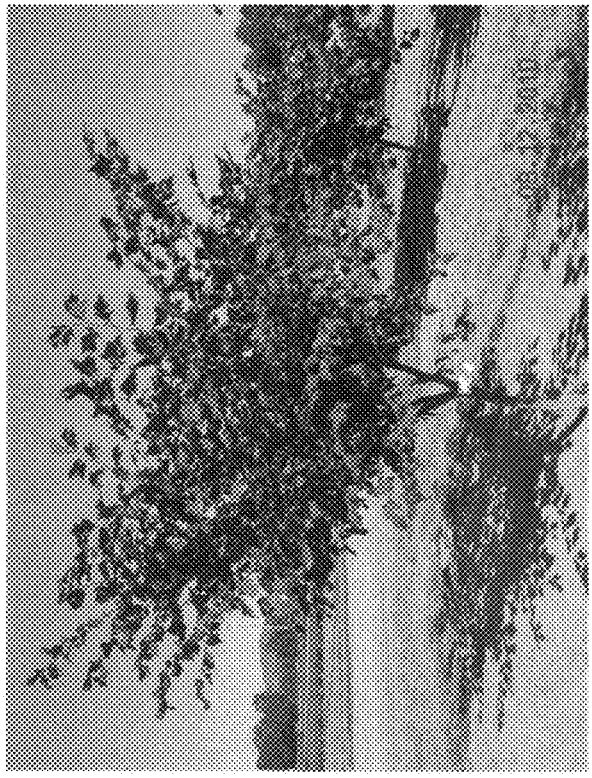
FIG. 6 is a digital image taken in mid-August of the $5^{th}$ growing season of the original 'Burgundy Lace' tree growing in Corvallis, Oreg., showing older leaves. Tree planted in the spring of 2007.
Figure 5:
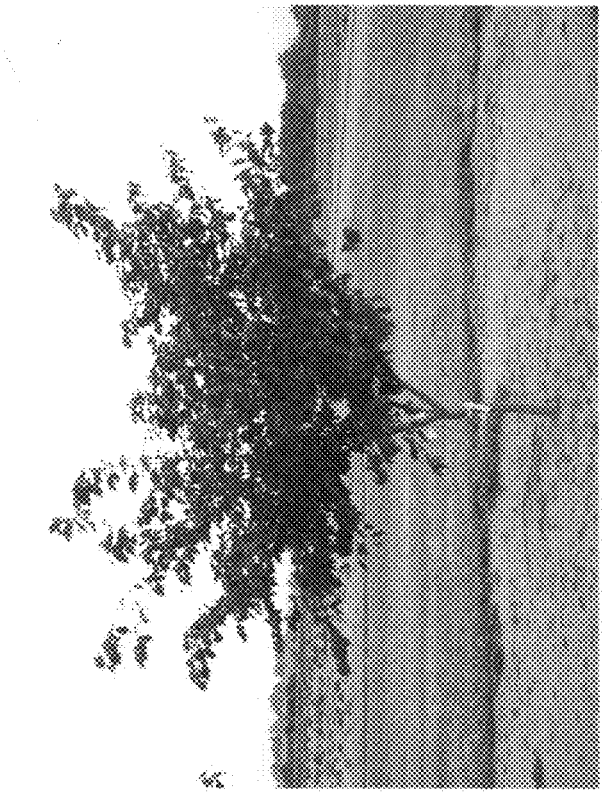
FIG. 5 is a digital image taken in June of the $5^{th}$ growing season of a tree of 'Burgundy Lace' growing in Corvallis, Oreg. Tree planted in the spring of 2007.
Figure 8:
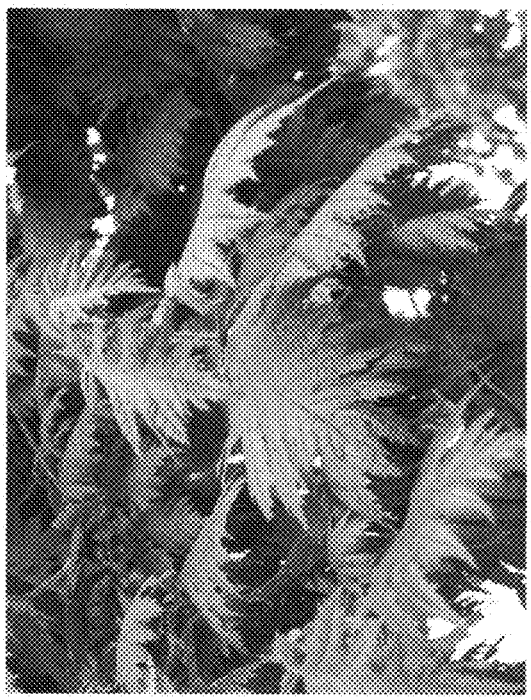
FIGS. 7-9 are digital images showing young leaves of 'Burgundy Lace' in Corvallis, Oreg. in late May.
Figure 7:
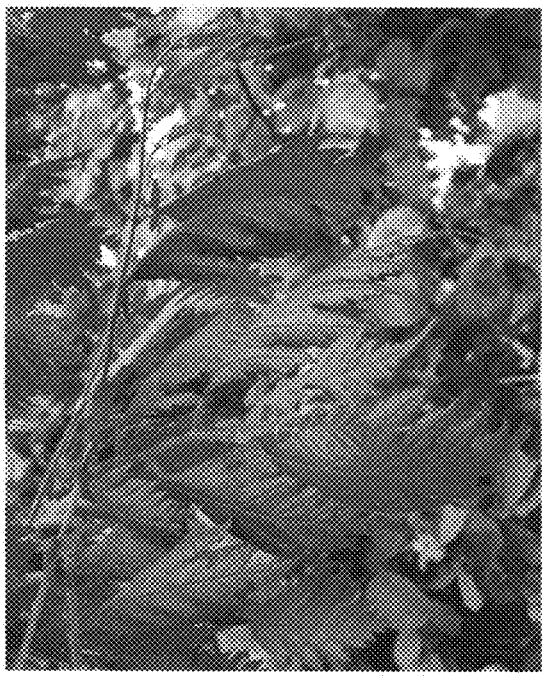
Figure 9:
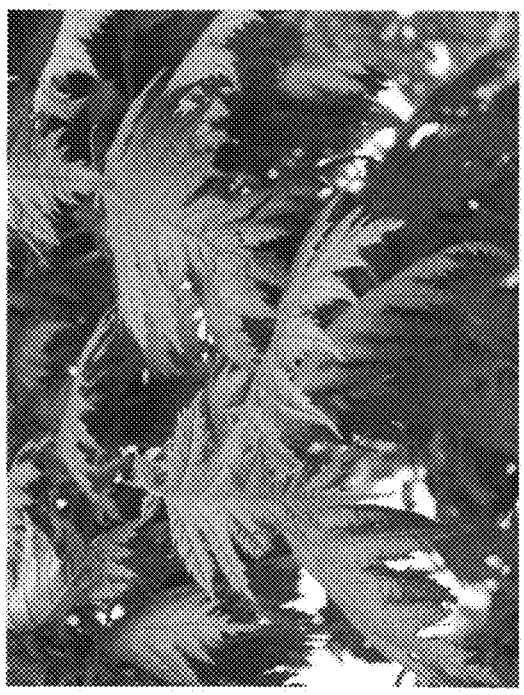
Figure 11:
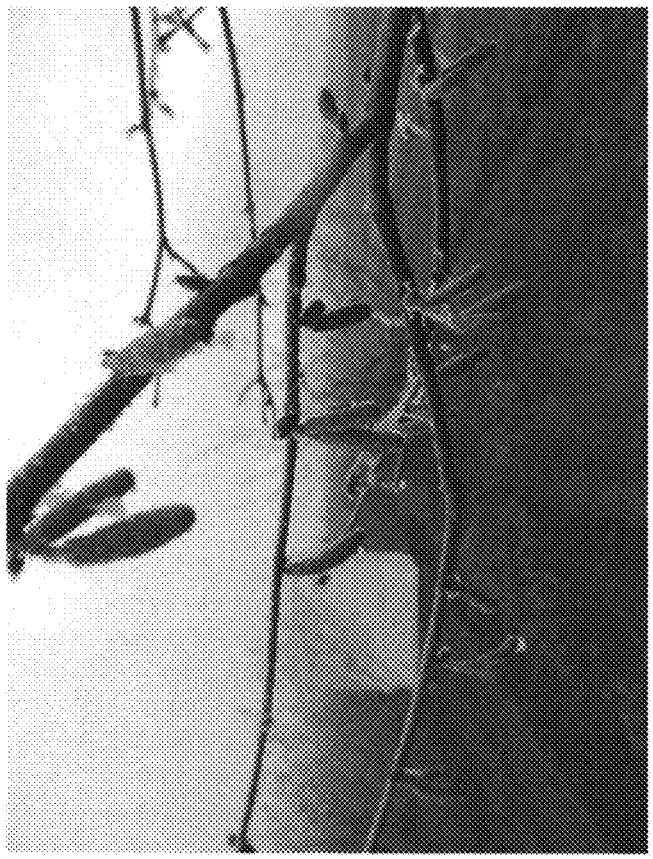
FIG. 11 is a digital image of catkins of 'Burgundy Lace' with frost.
Figure 10:
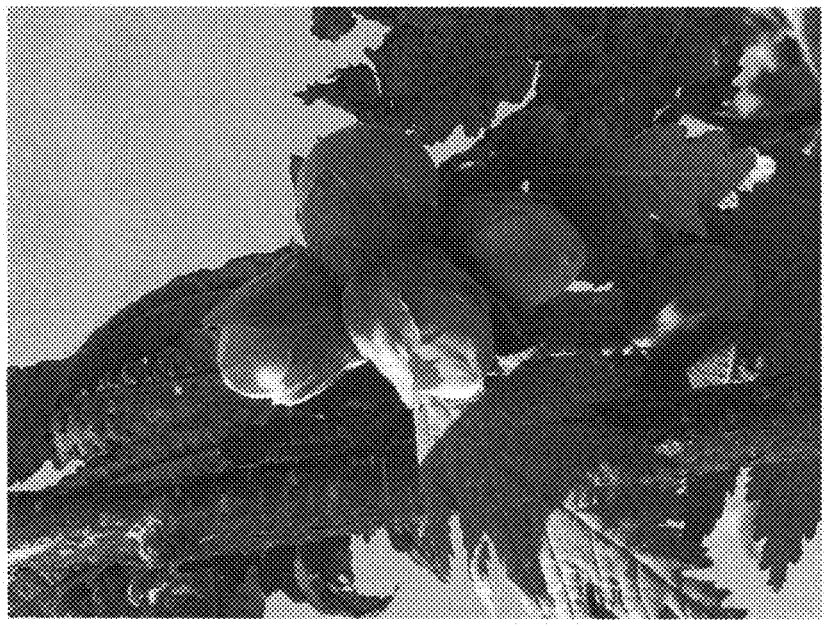
FIG. 10 is a digital image showing nuts and husks of 'Burgundy Lace' on a branch in Corvallis, Oreg. in August of the $4^{th}$ growing season.
Figure 13:
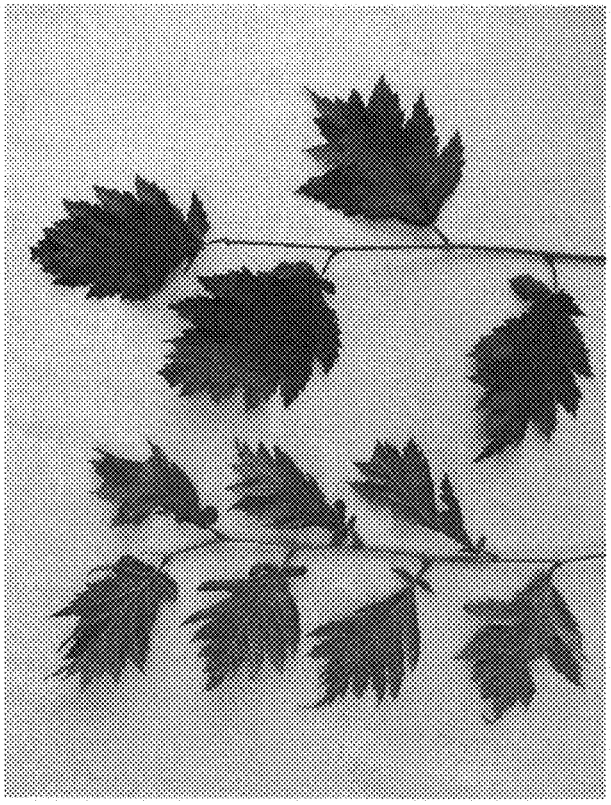
FIG. 13 is a digital image showing shoots of 'Burgundy Lace' grown in Corvallis, Oreg. showing upper and lower leaf surfaces.
Figure 12:
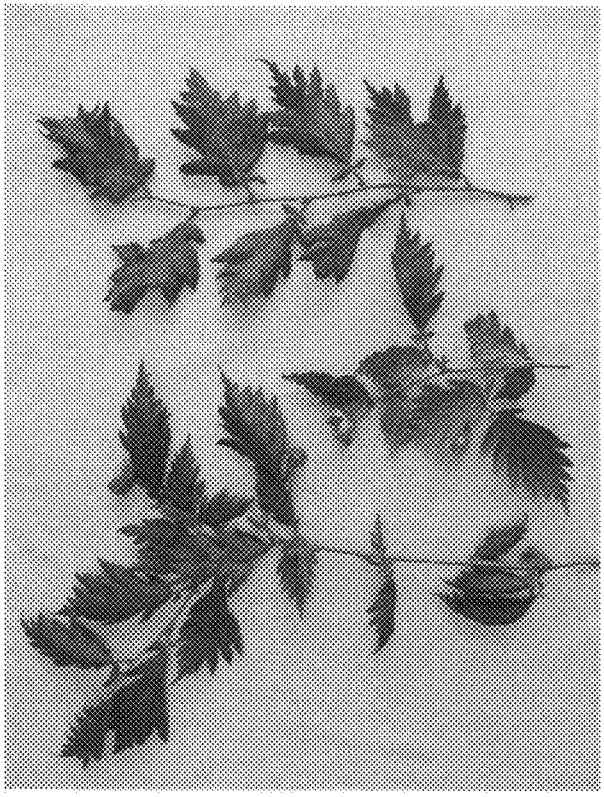
FIG. 12 is a digital image showing shoots of 'Burgundy Lace' grown in Corvallis, Oreg. with nuts.
Figure 14:
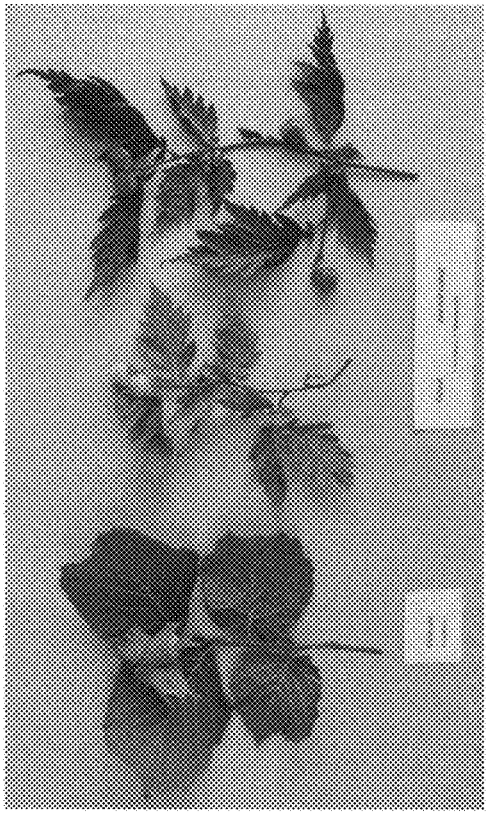
FIGS. 14-15 are digital images showing leaves, husks and nuts of 'Barcellona', 'Cutleaf' and 'Burgundy Lace' varieties.
Figure 15:
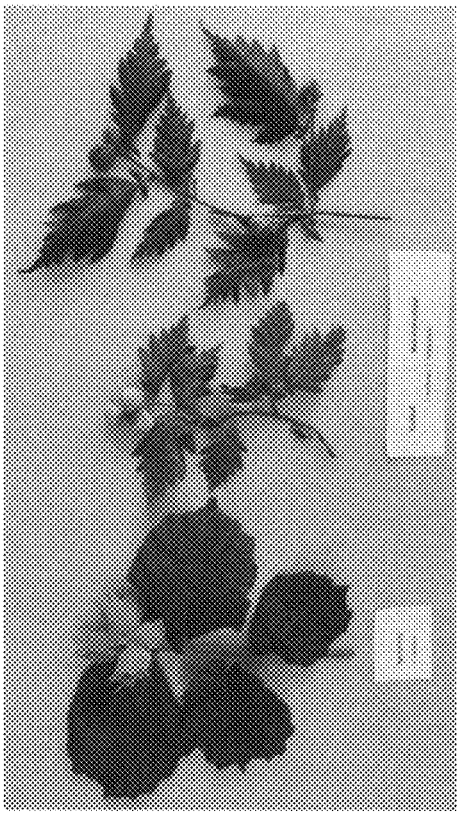
Figure 16:
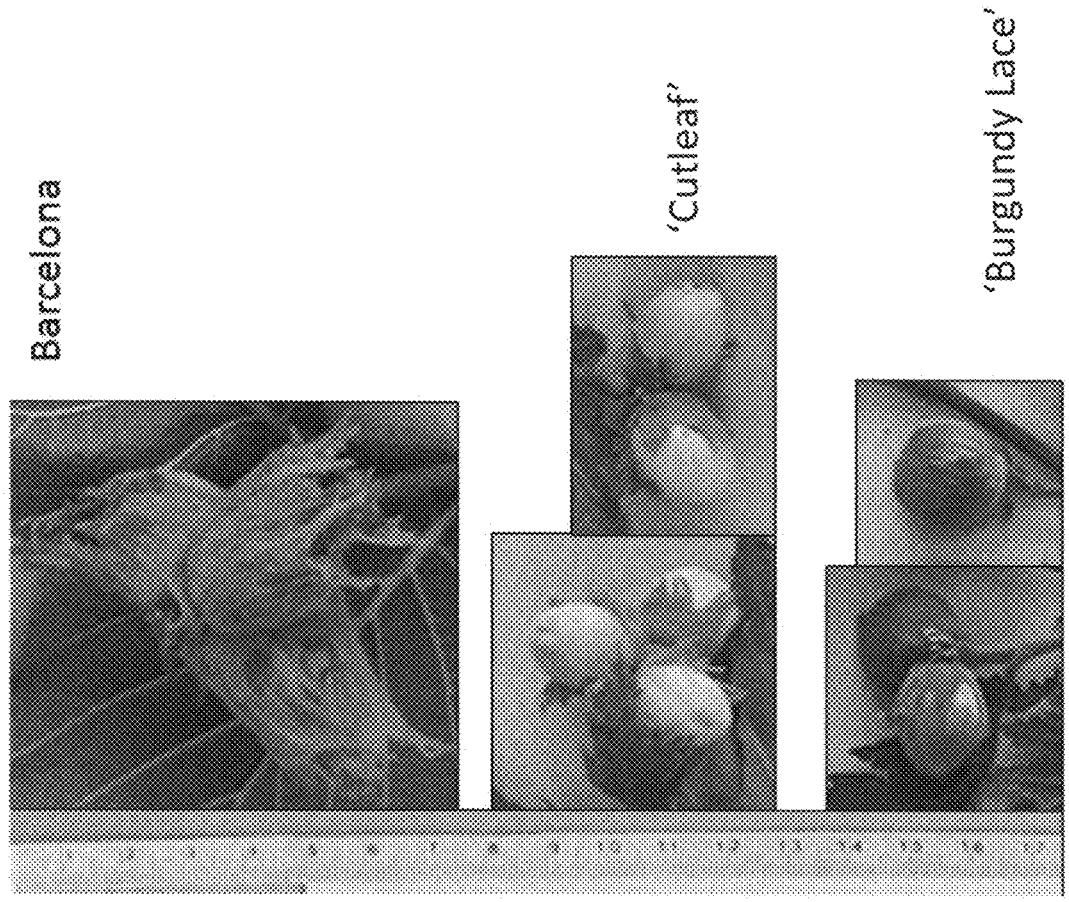
FIG. 16 is a digital image of comparing nuts of 'Barcelona', 'Cutleaf' and 'Burgundy Lace'.

The cultivar 'Burgundy Lace' has not been observed under all possible environmental conditions. The phenotype may vary somewhat with variations in environment such as temperature and light intensity, without, however, any variance in genotype. The aforementioned photographs and following observations and measurements describe plants grown in Corvallis, Oreg. under commercial practice outdoors in the field during the fall, winter and spring. Plants used for the photographs and description were propagated by tie-off layerage and growing on their own roots, and seven or eight years old. In the following description, color references are made to The Royal Horticultural Society Colour Chart, 1966 Edition, except where general terms of ordinary dictionary significance are used.

Botanical classification: *Corylus avellana* cultivar 'Burgundy Lace'.

Parentage:

- *Female, or seed, parent.*—*Corylus avellana* cultivar 'OSU 562.034' (unpatented).
- *Male, or pollen, parent.*—*Corylus avellana* cultivar 'OSU 562.062' (unpatented).

Propagation (type rooted suckers):

- *Time to initiate roots.*—About 30 days at 20° C.
- *Time to produce a rooted young plant.*—About six months at 22° C.
- *Root description.*—Fine to thick; freely branching; creamy white in color.

Propagation (type whip grafting):

- *Time to budbreak on the scions.*—About 14 days at 25° C.
- *Time to produce a grafted plant.*—About six months at 25° C.

Plant description:

- *General appearance.*—Perennial shrub. Upright-spreading plant habit.
- *Growth and branching habit.*—Freely branching; about 15 lateral branches develop per plant. Pinching, that is, removal of the terminal apices, enhances branching with lateral branches potentially forming at every node.
- *Vigor.*—Moderate vigor growth habit.
- *Size.*—Plant height is about 5 meters; plant diameter or spread is about 5 meters.

Lateral branch description:

- *Length.*—About 51 cm.
- *Diameter.*—About 3.8 mm.
- *Internode length.*—About 3.3 cm.
- *Texture.*—Smooth, glabrous.
- *Strength.*—Strong.
- *Color, immature.*—152B.
- *Color, mature.*—152B.

Foliage description:

- *Arrangement.*—Alternate, simple.
- *Length.*—About 11.4 cm.
- *Width.*—About 7.4 cm.
- *Shape.*—Cutleaf (deeply serrated).
- *Apex.*—Obtuse to acute.
- *Base.*—Cordate.
- *Margin.*—Deeply serrated.
- *Texture, upper and lower surfaces.*—Slightly pubescent.
- *Venation pattern.*—Pinnate.
- *Color.*—Developing foliage, upper surface 144A, lower surface 145A. Fully expanded foliage, upper surface: Spring and summer, 143A; late summer and fall, 143A. Fully expanded foliage, lower surface: Spring and summer, 139C; late summer and fall, 139C. Venation, upper surface: Spring and summer, 139C; late summer and fall, 139C. Venation, lower surface: Spring and summer, 139D; late summer and fall, 139D.

Petiole description:

- *Length.*—About 27 mm.
- *Diameter.*—About 1.8 mm.
- *Texture, upper and lower surfaces.*—Pubescent.
- *Color, upper surface.*—Spring and summer, 139D; late summer and fall, 139D.
- *Color, lower surface.*—Spring and summer, 139D; late summer and fall, 139D.

Flower description: Male inflorescences are catkins, color prior to elongation 194C. Female inflorescence style color 048B.

Nut description:

- *Length.*—About 19.1 mm.
- *Width.*—About 20.7 mm.
- *Depth.*—About 18.2 mm.
- *Nut shape.*—Round. Nut shape index [(Width+Depth)/2*Length]=1.02. Nut compression index (Width/Depth)=1.14.
- *Nut shell color.*—164B. Nut weight: About 1.72 grams.
- *Kernel weight.*—About 0.76 grams.
- *Kernel percentage* (*kernel weight/nut weight*).—About 44%.

Disease/pest resistance: Plants of the new *Corylus* are highly resistant to eastern filbert blight caused by the fungus *Anisogramma anomala* (Peck) E. Müller, although a few small cankers may develop under high disease pressure. Plants of the new *Corylus* are moderately susceptible to bud mites (*Phytoptus avellanae* Nal.), while plants of 'Tonda Gentile delle Langhe' are highly susceptible, and plants of 'Barcelona' are highly resistant.

Temperature tolerance: Plants of the new *Corylus* have been observed to tolerate temperatures from −21 to 38° C. in the field in Corvallis, Oreg.

Comparative data:

- *Tree size, growth habit, yield, and yield efficiency.*—Tree sizes in the trials were estimated by measuring trunk diameters 30 cm above the soil line, at the end of the $7^{th}$ growing season (December 2013 and 2014, respectively). Trunk cross-sectional area (TCA) was calculated from trunk diameter. Trees of 'Burgundy Lace' are moderately vigorous, similar in size to 'Jefferson' (Tables 1 & 2). In previous trials, TCAs of 'Jefferson' and 'Lewis' were about 70% of 'Barcelona'. Their upright-spreading growth habit of 'Burgundy Lace' trees should be easy to manage in a landscape setting. In the 2007 trial, total nut yield per tree averaged 10.04 kg for 'Burgundy Lace', which is less than the other four cultivars (Table 1). Nut yield efficiency for OSU 954.076 (0.122 kg/cm$^2$), which adjusts for differences in tree size, was similar to 'Felix' (0.133 kg/cm$^2$), and lower than 'Jefferson' (0.299 kg/cm$^2$), 'Santiam' (unpatented) (0.267 kg/cm$^2$) and 'McDonald' (0.245 kg/cm$^2$). In the 2008 trial, total nut yield per tree averaged 11.39 kg for 'Burgundy Lace', which is more than 'Eta' (unpatented) (7.78 kg) but less than the other 13 genotypes (Table 2). Nut yield efficiency for OSU 954.076 (0.134 kg/cm$^2$), which adjusts for differences in tree size, was similar to the pollinizer 'Theta' (unpatented) (0.149 kg/cm$^2$), higher than 'Eta' (0.100 kg/cm$^2$) and lower than 'Jefferson' (0.292 kg/cm$^2$) and the others in the trial. Although 'Burgundy Lace' would generally not be planted for nut production, its nuts show a very low frequency of defects (Tables 3 & 4). In the 2007 trial, nut weight was 1.72 g and kernel percentage was 44.1%, the latter being similar to 'Barcelona' (typically 43%). The amount of fiber on the pellicle was rated on a scale of 1 (no fiber) to 4 (heavy fiber) (Table 5). The rating for 'Burgundy Lace' (2.8) was similar to 'Jefferson' (3.0) and indicates a moderate amount of fiber. Kernel blanching, or ease with which the pellicle can be removed with dry heat followed by rubbing, was rated on a scale of 1 (complete pellicle removal) to 7 (no pellicle removal). The rating for 'Burgundy Lace' (6.6) indicates that very little of the pellicle is removed by dry heat. Very few moldy kernels were observed in 'Burgundy Lace' (0.5%), in striking contrast to 'Santiam' (17.3%) (Table 3). The results from the second trial (Table 4) were nearly identical: nut weight 1.71 g, kernel percentage 44%, fiber rating 2.8, blanching rating 6.6, with 87.5% good nuts and very few defects. The kernels, raw or roasted, are not attractive.

*Nut maturity date.*—Most nuts of 'Burgundy Lace' are borne in clusters of two, in husks about half as long as the nuts. The nuts are slightly long and compressed. The husks open as they dry at maturity, and about 98% of the nuts fall free of the husk. When mature, the shells are medium brown in color and have pubescence at the apical end. Harvest date is estimated to be three days before 'Barcelona'.

*Incompatibility and pollinizers.*—'Burgundy Lace' has incompatibility alleles $S_6$ and $S_{20}$ as determined by fluorescence microscopy. Both alleles are expressed in the females, but only $S_6$ is expressed in the pollen because of dominance. By convention, alleles expressed in the pollen are underlined. The trees set a moderate number of catkins. The catkins are abnormal and small, as are those of 'Cutleaf', and shed very little pollen. For practical purposes, 'Burgundy Lace' is male-sterile, although collection of a handful of catkins can give a trace of pollen. Time of pollen shed and female receptivity were observed weekly from December 2012 to March 2013 and December 2013 to March 2014 (FIG. 2). Female flower receptivity of 'Burgundy Lace' is late and about one week earlier than 'Cutleaf' and four weeks later than 'Barcelona'. Time of catkin elongation of 'Burgundy Lace' is also late and about three weeks earlier than 'Cutleaf' and three weeks later than 'Barcelona'. Date of leaf budbreak is about one week later than 'Cutleaf' and 2.5 weeks later than 'Barcelona'. Pollen of the following EFB-resistant cultivars is compatible on females of 'Burgundy Lace': 'Yamhill' ($S_8$ $S_{26}$), 'Dorris' ($S_1$ $S_{12}$), 'McDonald' ($S_2$ $S_{15}$), 'Wepster' ($S_1$ $S_2$), 'York' ($S_2$ $S_{21}$), 'Gamma' ($S_2$ $S_{10}$), 'Jefferson' ($S_1$ $S_3$), 'Felix' ($S_{15}$ $S_{21}$) and 'Theta' ($S_5$ $S_{15}$). Because females of 'Burgundy Lace' are receptive late in the season, the late-shedding pollinizers 'Felix' and 'Theta' are most effective.

*Pests and diseases.*—Based on DNA marker data, 'Burgundy Lace' has a very high level of resistance to EFB conferred by a dominant allele from 'Gasaway', so fungicide applications are not needed. RAPD markers 152-800 and 268-580 that flank the resistance allele in 'Gasaway', are present in 'Burgundy Lace'. Trees of 'Burgundy Lace' have not yet been challenged with the EFB pathogen in glasshouse or structure inoculations. Susceptibility to bacterial blight caused by *Xanthomonas campestris* pv. *corylina* has not been quantified, but none of the three trees in the two trials were affected. Nevertheless, copper sprays to minimize damage from this pathogen can be performed. Susceptibility to big bud mite (primarily *Phytoptus avellanae* Nal.) was rated in the 2007 trial (Table 3) after leaf fall once per year for five years (December 2009-2013). The scale was from 1 (no blasted buds) to 5 (many blasted buds). The average rating for 'Burgundy Lace' (3.0) is similar to that for 'Clark' and lower than for 'Cutleaf' (4.0), which was rated one year at the Smith Farm and three years (2000-2002) at the nearby USDA National Clonal Germplasm Repository. In the 2008 trial, the rating for 'Burgundy Lace' (3.1) is the same as for the moderately susceptible 'Clark' (3.0). The number of blasted buds for 'Burgundy Lace' is lower than 'Cutleaf' and sprays should not be necessary to control this pest. The other check cultivars in the two trials had lower bud mite ratings.

*Propagation.*—'Burgundy Lace' was propagated by tie-off layerage of the suckers of the original seedling tree in late June over five years (2005, 2006, 2008, 2011 and 2013). On average, 22 suckers were layered, with rooting rated good on 11 and fair on 7, poor on 3 and no roots on one. The size (caliper) was rated as medium to large in most years. Layers are moderately vigorous and root well, but have lower vigor and caliper than those of 'Jefferson' and 'Barcelona'.

*DNA fingerprinting.*—Primers used are shown in Table 6, and results shown in Table 7. 'Burgundy Lace' differs from 'Cutleaf' at 14 of 24 loci.

REFERENCES

Bassil N. V., Botta R., Mehlenbacher S. A. 2005a. Microsatellite markers in hazelnut: Isolation, characterization and cross-species amplification. J. Amer. Soc. Hort. Sci. 130: 543-549.

Bassil N. V., Botta R., Mehlenbacher S. A. 2005b. Additional microsatellite markers of the European hazelnut. Acta Hort. 686:105-110.

Bassil N., Boccacci P., Botta R., Postman J. and Mehlenbacher S. 2012. Nuclear and chloroplast microsatellite markers to assess genetic diversity and evolution in hazelnut species, hybrids and cultivars. Genetic Resources and Crop Evolution (on-line) DOI10.1007/s10722-012-9857-z Boccacci P., Akkak A., Bassil N. V., Mehlenbacher S. A., Botta R. 2005. Characterization and evaluation of microsatellite loci in European hazelnut (*C. avellana*) and their transferability to other *Corylus* species. Molec. Ecol. Notes 5:934-937.

Boccacci R, Akkak, A. and Botta, R. 2006. DNA typing and genetic relations among European hazelnut (*Corylus avellana* L.) cultivars using microsatellite markers. Genome 49:598-611.

Gökirmak T., Mehlenbacher S. A., Bassil N. V. 2009. Characterization of European hazelnut (*Corylus avellana*) cultivars using SSR markers. Genetic Resources and Crop Evolution 56:147-172.

Gürcan, K. and S. A. Mehlenbacher. 2010. Transferability of microsatellite markers in the Betulaceae. J. Amer. Soc. Hort. Sci. 135:159-173.

Gürcan, K. and S. A. Mehlenbacher. 2010. Development of microsatellite marker loci for European hazelnut (*Corylus avellana* L.) from ISSR fragments. Molecular Breeding 26:551-559.

Gürcan, K. and S. A. Mehlenbacher and V. Erdogan. 2010a. Genetic diversity in hazelnut cultivars from Black Sea countries assessed using SSR markers. Plant Breeding 129:422-434. (available on-line doi:10.1111/j.1439-0523.2009.01753.x).

Gürcan, K., S. A. Mehlenbacher, R. Botta and P. Boccacci. 2010b. Development, characterization, segregation, and mapping of microsatellite markers for European hazelnut (*Corylus avellana* L.) from enriched genomic libraries and usefulness in genetic diversity studies. Tree Genetics and Genomes 6:513-531. (available on-line as DOI:10.1007/s11295-010-0269-y)

Mehlenbacher et al., 2004. RAPD markers linked to eastern filbert blight resistance in *Corylus avellana*. Theor. Appl. Genet. 108:651-656.

Mehlenbacher and Smith. 1995. Inheritance of the cutleaf trait in hazelnut. HortScience 30:611-612.

Sathuvalli, V. R. and S. A. Mehlenbacher. 2012. Characterization of American hazelnut (*Corylus americana*) accessions and *Corylus americana*×*Corylus avellana* hybrids using microsatellite markers. Genetic Resources and Crop Evolution 59:1055-1075. DOI10.1007/s10722-011-9743-0.

TABLE 1

Nut yield, trunk cross-sectional area, yield efficiency and bud mite ratings of hazelnut cultivars and selections (including two trees of 'Burgundy Lace' in a guard row) in a trial planted in 2007.

| | No. | Yield per tree (kg) | | | | | | TCA[z] | YE[y] | |
|---|---|---|---|---|---|---|---|---|---|---|
| Cultivar | trees | Year 3 | Year 4 | Year 5 | Year 6 | Year 7 | Total | ($cm^2$) | ($kg \cdot cm^{-2}$) | BBM |
| 'McDonald' | 4 | 0.15 | 1.10 | 4.85 | 7.38 | 7.95 | 21.43 | 87.6 | 0.245 | 1.8 |
| 'Felix' | 4 | 0.06 | 1.04 | 2.91 | 7.93 | 4.95 | 16.88 | 128.4 | 0.133 | 2.0 |
| 'Jefferson' | 4 | 0.55 | 1.97 | 5.63 | 4.60 | 10.25 | 22.99 | 77.5 | 0.299 | 1.2 |
| 'Santiam' | 4 | 0.20 | 1.11 | 4.09 | 5.46 | 6.83 | 17.68 | 66.8 | 0.267 | 2.2 |
| $LSD_{0.05}$ | | 0.21 | 0.43 | 0.54 | 2.04 | 1.18 | 2.45 | 13.48 | 0.029 | 0.2 |
| 'Burgundy Lace' | 2 | 0.09 | 0.56 | 2.29 | 2.87 | 4.24 | 10.04 | 82.2 | 0.122 | 3.0 |

[z]Trunk cross-sectional area calculated from trunk diameters measured in late fall at the end of the 7th season.
[y]Yield efficiency = Total nut yield/TCA.

TABLE 2

Nut yield, trunk cross-sectional area, yield efficiency and bud mite ratings of hazelnut cultivars and selections in two trials planted in 2008.

| | | | Nut yield per tree (kg) | | | | | | | | |
|---|---|---|---|---|---|---|---|---|---|---|---|
| Selection | SelNo | No. trees | 2010 | 2011 | 2012 | 2013 | 2014 | Total | TCA[z] | YldEff[y] | BBM[x] |
| EFB-resistant selections | | | | | | | | | | | |
| 918.045 | 1 | 4 | 0.233 | 2.593 | 3.585 | 4.513 | 6.148 | 17.070 | 69.0 | 0.249 | 1.5 |
| 951.086 | 2 | 4 | 0.213 | 1.718 | 5.073 | 7.557 | 9.510 | 24.069 | 92.7 | 0.258 | 2.0 |
| 964.073 | 3 | 4 | 0.100 | 1.163 | 40.998 | 6.223 | 8.870 | 20.453 | 85.1 | 0.242 | 1.0 |
| 981.067 | 4 | 4 | 0.027 | 0.968 | 2.740 | 3.630 | 6.550 | 13.914 | 83.3 | 0.168 | 1.2 |
| 990.035 | 5 | 4 | 0.088 | 1.258 | 4.350 | 4.800 | 8.420 | 18.915 | 72.5 | 0.259 | 1.7 |
| 992.015 | 6 | 4 | 0.053 | 0.945 | 2.068 | 3.625 | 6.288 | 12.978 | 74.0 | 0.177 | 1.4 |
| 992.022 | 7 | 4 | 0.040 | 1.978 | 4.470 | 7.338 | 8.340 | 22.165 | 98.8 | 0.224 | 1.4 |
| 1014.058 | 8 | 4 | 0.210 | 3.580 | 3.148 | 5.538 | 6.368 | 18.843 | 74.0 | 0.256 | 2.3 |
| 1018.001 | 9 | 4 | 0.105 | 2.210 | 2.738 | 4.695 | 6.178 | 15.925 | 74.1 | 0.215 | 1.3 |
| Eta | 10 | 4 | 0.055 | 0.665 | 1.688 | 1.867 | 3.503 | 7.777 | 77.9 | 0.100 | 2.0 |
| Gamma | 11 | 4 | 0.153 | 0.780 | 3.310 | 5.133 | 8.240 | 17.615 | 97.6 | 0.181 | 2.9 |
| Jefferson | 12 | 4 | 0.223 | 2.650 | 4.793 | 5.875 | 8.570 | 22.110 | 75.9 | 0.292 | 1.2 |
| Theta | 13 | 4 | 0.038 | 1.240 | 4.003 | 4.910 | 4.560 | 14.750 | 101.7 | 0.149 | 1.6 |
| Yamhill | 14 | 4 | 0.218 | 2.833 | 4.793 | 6.805 | 8.698 | 23.345 | 73.7 | 0.318 | 1.1 |
| LSD 0.05 | | | 0.113 | 0.524 | 0.945 | 1.243 | 1.552 | 3.296 | 14.4 | 0.038 | 0.4 |
| Burgundy Lace | h | 1 | 0.020 | 1.480 | 2.270 | 3.110 | 4.510 | 11.390 | 84.9 | 0.134 | 3.1 |

TABLE 2-continued

Nut yield, trunk cross-sectional area, yield efficiency and bud mite ratings of hazelnut cultivars and selections in two trials planted in 2008.

| Selection | SelNo | No. trees | Nut yield per tree (kg) 2010 | 2011 | 2012 | 2013 | 2014 | Total | TCA[z] | YldEff[y] | BBM[x] |
|---|---|---|---|---|---|---|---|---|---|---|---|
| Performance of hazelnut cultivars and selections (including 'Burgundy Lace') in two trials planted in 2008. EFB-susceptible selections in nearby trial | | | | | | | | | | | |
| 919.031 | 1 | 3 | 0.050 | 1.547 | 4.890 | 5.200 | 8.057 | 19.743 | 102.0 | 0.195 | 1.0 |
| 961.021 | 2 | 3 | 0.225 | 1.527 | 3.507 | 4.770 | 7.793 | 17.821 | 91.1 | 0.196 | 2.5 |
| 961.063 | 3 | 3 | 0.153 | 1.707 | 2.707 | 3.937 | 4.490 | 12.993 | 56.4 | 0.231 | 1.7 |
| 978.057 | 4 | 3 | 0.227 | 1.553 | 3.063 | 5.710 | 5.037 | 15.590 | 83.3 | 0.189 | 2.9 |
| 978.058 | 5 | 3 | 0.207 | 1.533 | 3.297 | 5.025 | 7.633 | 17.695 | 88.1 | 0.201 | 1.7 |
| 978.064 | 6 | 3 | 0.190 | 2.083 | 2.790 | 4.270 | 4.387 | 13.720 | 57.7 | 0.238 | 1.0 |
| 1012.074 | 7 | 3 | 0.127 | 0.790 | 1.340 | 3.937 | 4.475 | 10.668 | 93.6 | 0.115 | 3.0 |
| Barcelona | 8 | 3 | 0.197 | 1.650 | 4.670 | 5.357 | 8.313 | 20.187 | 125.8 | 0.161 | 1.0 |
| Clark | 9 | 3 | 0.483 | 3.416 | 1.873 | 6.130 | 6.320 | 18.223 | 72.5 | 0.251 | 3.0 |
| Lewis | 10 | 3 | 0.370 | 3.350 | 2.210 | 7.643 | 6.833 | 20.407 | 80.0 | 0.255 | 2.7 |
| Sacajawea | 11 | 3 | 0.050 | 0.857 | 4.247 | 6.855 | 9.060 | 21.068 | 99.1 | 0.214 | 1.1 |
| LSD 0.05 | | | 0.185 | 0.580 | 0.866 | 0.942 | 1.569 | 2.811 | 16.7 | 0.028 | 0.4 |

[z]Trunk cross-sectional area calculated from trunk diameters measured in late fall at the end of the 7th season.

[y]Yield efficiency = Total nut yield/TCA.

[x]Susceptibility to bud mite (primarily *Phytoptus avellanae* Nal.) was rated on four trees of each selection on a scale of 1 (no blasted buds) to 5 (many blasted buds). Shown are mean ratings for 5 years (2010-2014). (many blasted buds). Shown are mean ratings for 5 years (2010-2014).

LSD = least significant difference.

TABLE 3

Frequency of good nuts, and of nut and kernel defects in hazelnut cultivars and selections (including two trees of 'Burgundy Lace' in a guard row) in a trial planted in 2007.

| Selection | # trees | Frequency (%)[z] Good | Blanks | Brown stain | Moldy | Shrivel | Poor fill | Twins | Black tips |
|---|---|---|---|---|---|---|---|---|---|
| 'McDonald' | 4 | 83.5 | 5.1 | 0.1 | 2.1 | 4.5 | 4.5 | 0.1 | 0.3 |
| 'Felix' | 4 | 88.9 | 4.2 | 0.2 | 2.1 | 0.4 | 2.9 | 0.3 | 1.1 |
| 'Jefferson' | 4 | 80.1 | 4.3 | 0.3 | 5.7 | 0.4 | 8.9 | 0.6 | 0.6 |
| 'Santiam' | 4 | 68.8 | 2.8 | 0.1 | 17.3 | 1.8 | 9.6 | 0.1 | 0.1 |
| LSD 0.05 | | 3.5 | 2.5 | 0.3 | 2.3 | 1.0 | 2.5 | 0.4 | 0.5 |
| 'Burgundy Lace' | 2 | 87.5 | 6.8 | 0.0 | 0.5 | 0.3 | 4.8 | 0.0 | 0.3 |

[z]Means of years 4-7.

LSD = Least Significant Difference

TABLE 4

Frequency of good nuts and of nut and kernel defects in hazelnut cultivars and selections in a trial planted in 2008.

| Selection | SelNo | # trees | 10-NutWt | 10-KerWt | PctKer | Fib | Blanch | GD | BL | BS | MO | SH | PF | TW | BT |
|---|---|---|---|---|---|---|---|---|---|---|---|---|---|---|---|
| EFB-resistant selections | | | | | | | | | | | | | | | |
| 918.045 | 1 | 4 | 25.81 | 11.69 | 45.31 | 1.5 | 3.9 | 73.26 | 4.18 | 0.56 | 2.18 | 0.44 | 18.38 | 1.06 | 0.12 |
| 951.086 | 2 | 4 | 27.88 | 12.43 | 44.54 | 2.2 | 5.4 | 82.92 | 5.86 | 0.64 | 1.78 | 0.08 | 11.22 | 0.58 | 0.50 |
| 964.073 | 3 | 4 | 26.09 | 12.33 | 47.20 | 2.2 | 4.7 | 82.20 | 1.80 | 0.14 | 1.34 | 1.26 | 13.14 | 0.00 | 0.26 |
| 981.067 | 4 | 4 | 23.97 | 11.38 | 47.53 | 3.7 | 3.9 | 90.62 | 4.32 | 0.18 | 0.56 | 0.18 | 2.82 | 1.26 | 0.06 |
| 990.035 | 5 | 4 | 23.90 | 11.34 | 47.56 | 1.6 | 4.7 | 75.11 | 3.50 | 0.06 | 2.94 | 1.26 | 15.62 | 1.32 | 0.44 |
| 992.015 | 6 | 4 | 24.33 | 12.32 | 50.71 | 2.6 | 4.5 | 85.06 | 7.56 | 0.18 | 2.06 | 0.50 | 4.06 | 0.12 | 0.76 |
| 992.022 | 7 | 4 | 26.50 | 12.82 | 48.41 | 3.2 | 3.8 | 80.32 | 4.62 | 0.00 | 3.18 | 0.82 | 10.76 | 0.18 | 0.26 |
| 1014.058 | 8 | 4 | 25.20 | 11.73 | 46.63 | 1.7 | 4.9 | 92.32 | 1.44 | 0.32 | 0.76 | 0.88 | 3.76 | 0.18 | 0.38 |
| 1018.001 | 9 | 4 | 25.60 | 12.05 | 47.17 | 2.9 | 3.8 | 83.68 | 4.88 | 0.06 | 4.18 | 0.18 | 6.62 | 0.50 | 0.12 |
| Eta | 10 | 4 | 30.21 | 14.21 | 47.12 | 3.1 | 3.9 | 85.86 | 2.80 | 1.80 | 2.06 | 0.40 | 5.74 | 1.00 | 0.66 |
| Gamma | 11 | 4 | 24.06 | 12.40 | 51.66 | 3.0 | 6.4 | 78.76 | 5.18 | 0.68 | 2.18 | 1.38 | 11.50 | 0.26 | 0.12 |
| Jefferson | 12 | 4 | 36.51 | 16.48 | 45.23 | 2.9 | 4.5 | 75.56 | 4.06 | 0.12 | 5.82 | 0.38 | 13.12 | 0.62 | 1.18 |
| Theta | 13 | 4 | 22.73 | 11.48 | 50.52 | 2.2 | 2.6 | 89.06 | 2.38 | 0.26 | 1.76 | 0.32 | 5.82 | 0.26 | 0.26 |
| Yamhill | 14 | 4 | 23.59 | 11.13 | 47.26 | 1.4 | 5.1 | 76.00 | 2.32 | 0.12 | 2.50 | 0.82 | 18.44 | 0.06 | 0.26 |
| LSD 0.05 | | | 0.94 | 0.34 | 0.77 | 0.2 | 0.4 | 3.58 | 2.56 | 0.56 | 1.22 | 0.74 | 3.38 | 0.48 | 0.08 |
| 'Burgundy Lace' | | 1 | 17.16 | 7.56 | 44.08 | 2.8 | 6.6 | 87.50 | 6.75 | 0.00 | 0.50 | 0.25 | 4.75 | 0.00 | 0.25 |

TABLE 4-continued

Frequency of good nuts and of nut and kernel defects in hazelnut cultivars and selections in a trial planted in 2008.

| Selection | SelNo | | NutWt | KerWt | PctKer | Fib | Blanch | GD | BL | BS | MO | SH | PF | TW | BT |
|---|---|---|---|---|---|---|---|---|---|---|---|---|---|---|---|
| EFB-susceptible selections in nearby trial | | | | | | | | | | | | | | | |
| 919.031 | 1 | 3 | 26.53 | 13.55 | 51.15 | 2.3 | 2.1 | 81.50 | 4.30 | 0.40 | 1.60 | 0.60 | 11.20 | 0.00 | 0.40 |
| 961.021 | 2 | 3 | 25.53 | 12.00 | 46.99 | 1.3 | 3.5 | 84.26 | 4.76 | 0.16 | 2.00 | 3.34 | 4.76 | 0.66 | 0.26 |
| 961.063 | 3 | 3 | 25.87 | 12.25 | 47.48 | 1.9 | 2.6 | 88.84 | 2.16 | 0.76 | 1.84 | 0.58 | 4.34 | 1.42 | 0.34 |
| 978.057 | 4 | 3 | 29.38 | 13.91 | 47.42 | 3.1 | 3.0 | 83.50 | 8.00 | 0.00 | 2.66 | 1.00 | 4.16 | 0.26 | 0.76 |
| 978.058 | 5 | 3 | 30.98 | 14.78 | 47.71 | 2.6 | 2.6 | 85.82 | 4.36 | 0.36 | 1.46 | 1.00 | 5.18 | 0.72 | 1.18 |
| 978.064 | 6 | 3 | 25.62 | 13.13 | 51.22 | 2.2 | 3.3 | 74.50 | 7.58 | 0.08 | 3.76 | 6.66 | 5.92 | 0.16 | 1.66 |
| 1012.074 | 7 | 3 | 23.17 | 11.84 | 51.08 | 2.1 | 2.2 | 89.36 | 3.64 | 0.64 | 1.82 | 0.64 | 3.46 | 0.18 | 0.36 |
| Barcelona | 8 | 3 | 38.87 | 17.08 | 44.00 | 2.5 | 4.3 | 68.26 | 5.26 | 0.16 | 4.00 | 1.42 | 16.00 | 6.00 | 0.16 |
| Clark | 9 | 3 | 24.73 | 12.41 | 50.02 | 2.6 | 3.1 | 73.08 | 2.58 | 1.00 | 4.00 | 0.50 | 18.34 | 0.84 | 0.34 |
| Lewis | 10 | 3 | 29.41 | 13.60 | 46.20 | 1.3 | 4.1 | 65.26 | 2.00 | 0.16 | 11.00 | 1.26 | 19.66 | 2.00 | 0.76 |
| Sacajawea | 11 | 3 | 28.07 | 14.55 | 51.85 | 1.3 | 3.1 | 82.72 | 4.90 | 0.00 | 4.72 | 2.10 | 5.00 | 0.18 | 0.54 |
| LSD 0.05 | | | 1.64 | 0.67 | 0.72 | 0.3 | 0.3 | 5.94 | 2.02 | 0.70 | 1.60 | 1.10 | 6.36 | 0.78 | 0.50 |
| 919.031 | 1 | 3 | 26.53 | 13.55 | 51.15 | 2.3 | 2.1 | 81.50 | 4.30 | 0.40 | 1.60 | 0.60 | 11.20 | 0.00 | 0.40 |
| 961.021 | 2 | 3 | 25.53 | 12.00 | 46.99 | 1.3 | 3.5 | 84.26 | 4.76 | 0.16 | 2.00 | 3.34 | 4.76 | 0.66 | 0.26 |
| 961.063 | 3 | 3 | 25.87 | 12.25 | 47.48 | 1.9 | 2.6 | 88.84 | 2.16 | 0.76 | 1.84 | 0.58 | 4.34 | 1.42 | 0.34 |
| 978.057 | 4 | 3 | 29.38 | 13.91 | 47.42 | 3.1 | 3.0 | 83.50 | 8.00 | 0.00 | 2.66 | 1.00 | 4.16 | 0.26 | 0.76 |
| 978.058 | 5 | 3 | 30.98 | 14.78 | 47.71 | 2.6 | 2.6 | 85.82 | 4.36 | 0.36 | 1.46 | 1.00 | 5.18 | 0.72 | 1.18 |
| 978.064 | 6 | 3 | 25.62 | 13.13 | 51.22 | 2.2 | 3.3 | 74.50 | 7.58 | 0.08 | 3.76 | 6.66 | 5.92 | 0.16 | 1.66 |
| 1012.074 | 7 | 3 | 23.17 | 11.84 | 51.08 | 2.1 | 2.2 | 89.36 | 3.64 | 0.64 | 1.82 | 0.64 | 3.46 | 0.18 | 0.36 |
| Barcelona | 8 | 3 | 38.87 | 17.08 | 44.00 | 2.5 | 4.3 | 68.26 | 5.26 | 0.16 | 4.00 | 1.42 | 16.00 | 6.00 | 0.16 |
| Clark | 9 | 3 | 24.73 | 12.41 | 50.02 | 2.6 | 3.1 | 73.08 | 2.58 | 1.00 | 4.00 | 0.50 | 18.34 | 0.84 | 0.34 |
| Lewis | 10 | 3 | 29.41 | 13.60 | 46.20 | 1.3 | 4.1 | 65.26 | 2.00 | 0.16 | 11.00 | 1.26 | 19.66 | 2.00 | 0.76 |
| Sacajawea | 11 | 3 | 28.07 | 14.55 | 51.85 | 1.3 | 3.1 | 82.72 | 4.90 | 0.00 | 4.72 | 2.10 | 5.00 | 0.18 | 0.54 |
| LSD 0.05 | | | 1.64 | 0.67 | 0.72 | 0.3 | 0.3 | 5.94 | 2.02 | 0.70 | 1.60 | 1.10 | 6.36 | 0.78 | 0.50 |

Notes (%):
GD = good kernels, BL = blanks, BS = brown stain, MO = moldy kernels, SH = shriveled kernels, PF = poorly filled nuts, TW = twins, BT = black tips.

TABLE 5

Ten-nut and 10-kernel weight, kernel percentage, and ratings for fiber and blanching for hazelnut cultivars and selections (including 'Burgundy Lace') in a trial planted in 2007.

| Selection | No. trees | 10-nut wt | 10-ker wt | Kernel percentage | Fiber[y] | Blanching[x] |
|---|---|---|---|---|---|---|
| McDonald | 4 | 26.2 | 13.7 | 52.3 | 2.6 | 3.3 |
| Felix | 4 | 27.1 | 13.7 | 50.8 | 3.0 | 2.2 |
| Jefferson | 4 | 37.6 | 16.7 | 44.5 | 3.0 | 4.3 |
| Santiam | 4 | 22.8 | 11.5 | 50.6 | 3.0 | 4.2 |
| LSD $_{0.05}$ | | 2.2 | 0.4 | 1.0 | 0.1 | 0.4 |

TABLE 5-continued

Ten-nut and 10-kernel weight, kernel percentage, and ratings for fiber and blanching for hazelnut cultivars and selections (including 'Burgundy Lace') in a trial planted in 2007.

| Selection | No. trees | 10-nut wt | 10-ker wt | Kernel percentage | Fiber[y] | Blanching[x] |
|---|---|---|---|---|---|---|
| 'Burgundy Lace | 2 | 17.2 | 7.6 | 44.1 | 2.8 | 6.6 |

[z]Means for nuts and kernels are over four years.
[y]Amount of fiber on the pellicle was rated in the second trial from 1 (none) to 4 (much).
[x]Blanching was rated from 1 (complete pellicle removal) to 7 (no pellicle removal).
LSD = least significant difference.

TABLE 6

Primers, annealing temperatures, and characterisitics for the 24 microsatellite marker loci used to fingerprint 'Burgundy Lace' and other hazelnut cultivars.

| Locus | Repeat Motif | Allele sizes | Primers (5'-3') (forward above, reverse below) | Tm (° C.) | n | He | Ho | PIC | r | LG | Locus | Reference |
|---|---|---|---|---|---|---|---|---|---|---|---|---|
| A613 | $(TC)_{13}(CA)_{12}$ | 149-177 | Ned-CACACGCCTT GTCACTCTTT (SEQ ID NO: 1) CCCCTTTCAC ATGTTTGCTT (SEQ ID NO: 2) | 60 | 14 | 0.86 | 0.85 | 0.85 | 0.00 | 11R | A613 | Gurcan et al. 2010 |
| A614 | $(TC)_{17}(CA)_{10}$ NNN$(CA)_{6}$ | 125-156 | Hex-TGGCAGAGCT TTGTCAGCTT (SEQ ID NO: 3) GCAGTGGAGG ATTGCTGACT (SEQ ID NO: 4) | 60 | 14 | 0.85 | 0.85 | 0.84 | 0.00 | 6S, 6R | A614 | Gurcan et al. 2010 |

TABLE 6-continued

Primers, annealing temperatures, and characterisitics for the 24 microsatellite marker loci used to fingerprint 'Burgundy Lace' and other hazelnut cultivars.

| Locus | Repeat Motif | Allele sizes | Primers (5'-3') (forward above, reverse below) | Tm (° C.) | n | He | Ho | PIC | r | LG | Locus | Reference |
|---|---|---|---|---|---|---|---|---|---|---|---|---|
| A616 | $(AC)_{11}$ | 136-162 | Fam-CACTCATACC GCAAACTCCA (SEQ ID NO: 5) ATGGCTTTTG CTTCGTTTTG (SEQ ID NO: 6) | 60 | 13 | 0.85 | 0.85 | 0.83 | 0.00 | 8R | A616 | Gurcan et al. 2010 |
| A640 | $(CT)_{15}(CA)_{13}$ | 354-378 | F-TGCCTCTGCA GTTAGTCAT (SEQ ID NO: 7) Fam-CGCCATATAATTG GGATGCTTGTTG (SEQ ID NO: 8) | 67 | 11 | 0.80 | 0.73 | 0.77 | 0.04 | 10R | A640 | Gurcan et al. 2010 |
| B617 | $(GA)_{15}$ | 280-298 | Fam-TCCGTGTTGA GTATGGACGA (SEQ ID NO: 9) TGTTTTTGGT GGAGCGATG (SEQ ID NO: 10) | 60 | 9 | 0.80 | 0.78 | 0.78 | 0.01 | 8S, 8R | B617 | Gurcan et al. 2010 |
| B619 | $(TC)_{21}$ | 146-180 | Fam-AGTCGGCTCC CCTTTTCTC (SEQ ID NO: 11) GCGATCTGAC CTCATTTTTG (SEQ ID NO: 12) | 60 | 14 | 0.88 | 0.88 | 0.87 | 0.00 | 3S, 3R | B619 | Gurcan et al. 2010 |
| B634 | $(AG)_{15}$ | 218-238 | Hex-CCTGCATCCA GGACTCATTA (SEQ ID NO: 13) GTGCAGAGGT TGCACTCAAA (SEQ ID NO: 14) | 60 | 9 | 0.76 | 0.76 | 0.73 | 0.00 | 4R | B634 | Gurcan et al. 2010 |
| B657 | $(AG)_{15}$ | 210-228 | Ned-GAGAGTGCGT CTTCCTCTGG (SEQ ID NO: 15) AGCCTCACCT CCAACGAAC (SEQ ID NO: 16) | 60 | 8 | 0.84 | 0.98 | 0.82 | −0.08 | 11S, 1 1R | B657 | Gurcan et al. 2010 |
| B662 | $(TC)_{15}$ | 220-236 | Hex-CGAAAGATGGA CTTCCATGAC (SEQ ID NO: 17) CAAGTTGAGAT TCTTCCTGCAA (SEQ ID NO: 18) | 60 | 9 | 0.74 | 0.68 | 0.72 | 0.04 | 3R | B662 | Gurcan et al. 2010 |
| B671 | $(AG)_{6}NN(GA)_{17}$ | 221-249 | Hex-TTGCCAGT GCATACTC (SEQ ID NO: 19) ACCAGCTCTG GGCTTAACAC (SEQ ID NO: 20) | 60 | 13 | 0.86 | 0.88 | 0.84 | −0.01 | 9S, 9R | B671 | Gurcan et al. 2010 |

TABLE 6-continued

Primers, annealing temperatures, and characterisitics for the 24 microsatellite marker loci used to fingerprint 'Burgundy Lace' and other hazelnut cultivars.

| Locus | Repeat Motif | Allele sizes | Primers (5'-3') (forward above, reverse below) | Tm (° C.) | n | He | Ho | PIC | r | LG | Locus | Reference |
|---|---|---|---|---|---|---|---|---|---|---|---|---|
| B709 | $(GA)_{21}$ | 219-233 | Ned-CCAAGCACGA ATGAACTCAA (SEQ ID NO: 21) GCGGGTTCTC GTTGTACACT (SEQ ID NO: 22) | 60 | 8 | 0.74 | 0.76 | 0.70 | −0.01 | 5S, 5R | B709 | Gurcan et al. 2010 |
| B733 | $(TC)_{15}$ | 161-183 | Ned-CACCCTCTTC ACCACCTCAT (SEQ ID NO: 23) CATCCCCTGT TGGAGTTTTC (SEQ ID NO: 24) | 60 | 8 | 0.68 | 0.68 | 0.63 | 0.00 | 7S, 2R | B733 | Gurcan et al. 2010 |
| B741 | $(GT)_5(GA)_{12}$ | 176-194 | Fam-GTTCACAGGC TGTTGGGTTT (SEQ ID NO: 25) CGTGTTGCTC ATGTGTTGTG (SEQ ID NO: 26) | 60 | 10 | 0.77 | 0.78 | 0.74 | 0.00 | 5S, 5R | B741 | Gurcan et al. 2010 |
| B749 | $(TC)_{12}$ | 200-210 | Hex-GGCTGACAAC ACAGCAGAAA (SEQ ID NO: 27) TCGGCTAGGG TTAGGGTTTT (SEQ ID NO: 28) | 60 | 6 | 0.60 | 0.64 | 0.51 | −0.03 | 1R | B749 | Gurcan et al. 2010 |
| B751 | $(GA)_{15}$ | 141-153 | Fam-AGCTGGTTCT TCGACATTCC (SEQ ID NO: 29) AAACTCAAATAA AACCCCTGCTC (SEQ ID NO: 30) | 60 | 7 | 0.80 | 0.78 | 0.77 | 0.01 | 7S, 2R | B751 | Gurcan et al. 2010 |
| B767 | $(TC)_{15}(AT)_7$ | 198-238 | Fam-CCACCAACTG TTTCACACCA (SEQ ID NO: 31) GCGAAATGGA GCTCTTGAAC (SEQ ID NO: 32) | 60 | 16 | 0.87 | 0.80 | 0.86 | 0.04 | 8S, 8R | B767 | Gurcan et al. 2010 |
| B774 | $(AG)_{15}$ | 195-213 | Ned-GTTTTGCGAG CTCATTGTCA (SEQ ID NO: 33) TGTGTGTGGTC TGTAGGCACT (SEQ ID NO: 34) | 60 | 8 | 0.80 | 0.80 | 0.77 | 0.00 | 5S, 5R | B774 | Gurcan et al. 2010 |
| B795 | $(TC)_8Ns(CT)_7Ns(CT)_{10}Ns(TC)_5$ | 296-332 | Fam-GACCCACAAACA ATAACCTATCTC (SEQ ID NO: 35) TGGGCATCAT CCAGGTCTA (SEQ ID NO: 36) | 60 | 12 | 0.76 | 0.74 | 0.74 | 0.01 | NA | B795 | Gurcan et al. 2010 |

TABLE 6-continued

Primers, annealing temperatures, and characterisitics for the 24 microsatellite marker loci used to fingerprint 'Burgundy Lace' and other hazelnut cultivars.

| Locus | Repeat Motif | Allele sizes | Primers (5'-3') (forward above, reverse below) | Tm (° C.) | n | He | Ho | PIC | r | LG | Locus | Reference |
|---|---|---|---|---|---|---|---|---|---|---|---|---|
| C115 | $(TAA)_5(GAA)_{12}$ | 167-225 | Fam-CATTTTCCGCA GATAATACAGG (SEQ ID NO: 37) GTTTCCAGATCTG CCTCCATATAAT (SEQ ID NO: 38) | 60 | 10 | 0.84 | 0.90 | 0.82 | −0.035 | 4S, 4R | C115 | Bassil 2005b; Gokirmak et al. 2009 |
| KG807 | $(TAAA)AA(TAAA)_2A(TAAA)_2$ | 226-248 | AAGCAAGAA AGGGATGGT (SEQ ID NO: 39) Fam-CTTACAGATAA ATGGCTCAAA (SEQ ID NO: 40) | 54 | 4 | 0.67 | 0.78 | 0.60 | −0.07 | 11 | KG807 | Gurcan and Mehlenbacher, 2010 |
| KG809 | $(AGG)_6$ | 333-345 | GGAAGGTGAGA GAAATCAAGT (SEQ ID NO: 41) Hex-AGGCATCAG TTCATCCAA (SEQ ID NO: 42) | 55 | 5 | 0.66 | 0.64 | 0.60 | 0.01 | 4 | KG809 | Gurcan and Mehlenbacher, 2010 |
| KG811 | $(GA)_{17}$ | 240-278 | GAACAACTGAA GACAGCAAAG (SEQ ID NO: 43) Ned-AAGGCGGCA CTCGCTCAC (SEQ ID NO: 44) | 58 | 12 | 0.83 | 0.82 | 0.81 | 0.01 | 2 | KG811 | Gurcan and Mehlenbacher, 2010 |
| KG827 | $(CT)_{13}AA(CA)_7$ | 264-282 | Fam-AGAACTCCGACTAAT AATCCTAACCCTTGC (SEQ ID NO: 45) GAGGGAGCAAGTCA AAGTTGAGAAGAAA (SEQ ID NO: 46) | 67 | 9 | 0.78 | 0.84 | 0.75 | −0.04 | 9 | KG827 | Gurcan and Mehlenbacher, 2010 |
| KG830 | $(CT)_{14}GTATT(CA)_8$ | 279-311 | Ned-TGGAGGAAGTTTTGA ATGGTAGTAGAGGA (SEQ ID NO: 47) AAAGCAACTCATAG CTGAAGTCCAATCA (SEQ ID NO: 48) | 67 | 9 | 0.79 | 0.78 | 0.76 | 0.00 | 9 | KG830 | Gurcan and Mehlenbacher, 2010 |

Primers fluorescent tags are FAM, HEX and NED
Tm annealing temperature (° C.); n number of alleles; He expected heterozygosity;
Ho observed heterozygosity; PIC polymorphism information content;
r estimated null allele frequency; LG linkage group; NA = not yet assigned
Reference for development and characterization

TABLE 7

Allele sizes in 'Burgundy Lace' and 12 other hazelnut cultivars at 24 microsatellite loci.

| Marker | Burgundy Lace | Cutleaf | Gasaway | Rode Zeller | Tonda G.d. Langhe | Barcelona | Yamhill | Dorris | Wepster | McDonald | York | Felix | Theta |
|---|---|---|---|---|---|---|---|---|---|---|---|---|---|
| A640 | 372/372 | 368/372 | 362/368 | 355/355 | 355/368 | 355/374 | 355/368 | 372/374 | 368/374 | 362/368 | 363/374 | 368/372 | 362/368 |
| B662 | 232/232 | 228/232 | 232/238 | 232/232 | 232/232 | 232/232 | 232/232 | 228/232 | 232/232 | 232/232 | 232/232 | 232/232 | 228/232 |
| KG809 | 339/339 | 339/339 | 339/348 | 342/345 | 339/342 | 339/339 | 348/348 | 339/348 | 342/342 | 339/339 | 339/348 | 339/348 | 339/348 |
| B774 | 207/213 | 207/213 | 203/209 | 203/207 | 203/211 | 203/207 | 203/211 | 203/207 | 203/207 | 203/213 | 203/209 | 203/213 | 203/213 |

TABLE 7-continued

Allele sizes in 'Burgundy Lace' and 12 other hazelnut cultivars at 24 microsatellite loci.

| Marker | Burgundy Lace | Cutleaf | Gasaway | Rode Zeller | Tonda G.d. Langhe | Barcelona | Yamhill | Dorris | Wepster | McDonald | York | Felix | Theta |
|---|---|---|---|---|---|---|---|---|---|---|---|---|---|
| B619 | 158/158 | 158/166 | 172/176 | 168/178 | 150/166 | 158/172 | 158/172 | 158/166 | 166/172 | 158/172 | 158/166 | 158/166 | 158/166 |
| B767 | 214/240 | 212/214 | 214/214 | 212/216 | 214/218 | 214/240 | 214/238 | 214/218 | 200/242 | 200/214 | 236/238 | 214/214 | 212/214 |
| B617 | 289/293 | 291/293 | 291/295 | 281/291 | 285/295 | 285/289 | 289/295 | 287/295 | 293/295 | 293/293 | 287/289 | 287/287 | 281/285 |
| A614 | 152/158 | 152/152 | 143/158 | 150/150 | 125/135 | 125/132 | 132/158 | 132/158 | 135/158 | 135/158 | 124/158 | 138/143 | 138/158 |
| B749 | 205/209 | 205/205 | 207/209 | 207/209 | 207/209 | 209/209 | 209/209 | 207/207 | 207/209 | 207/209 | 209/209 | 207/207 | 209/209 |
| B733 | 167/167 | 167/167 | 175/175 | 175/175 | 173/175 | 173/175 | 181/185 | 173/181 | 173/175 | 173/175 | 173/181 | 175/181 | 163/181 |
| B709 | 223/229 | 223/229 | 229/229 | 229/229 | 229/229 | 227/235 | 229/229 | 229/229 | 229/235 | 227/229 | 229/233 | 229/233 | 229/229 |
| KG830 | 293/303 | 297/305 | 291/305 | 303/303 | 291/295 | 291/295 | 291/295 | 295/297 | 295/305 | 291/295 | 295/295 | 293/303 | 297/297 |
| A616 | 144/156 | 152/156 | 150/150 | 144/148 | 150/152 | 144/152 | 150/150 | 150/152 | 152/160 | 150/160 | 144/152 | 150/152 | 132/134 |
| C115 | 216/216 | 216/216 | 216/219 | 194/216 | 174/174 | 174/194 | 197/216 | 194/216 | 183/194 | 174/197 | 197/197 | 197/216 | 197/216 |
| KG827 | 274/282 | 272/272 | 272/282 | 272/282 | 268/278 | 282/284 | 268/282 | 272/284 | 270/282 | 272/284 | 268/272 | 272/284 | 270/272 |
| B671 | 241/251 | 225/237 | 237/249 | 249/249 | 239/243 | 225/229 | 225/243 | 229/249 | 239/249 | 229/237 | 243/249 | 229/237 | 229/249 |
| A613 | 161/179 | 179/179 | 161/163 | 153/167 | 153/153 | 153/161 | 153/163 | 151/169 | 167/167 | 153/169 | 159/179 | 151/153 | 167/179 |
| KG811 | 257/257 | 255/257 | 257/261 | 255/257 | 257/267 | 261/267 | 251/261 | 257/267 | 257/257 | 245/267 | 257/257 | 251/267 | 257/257 |
| B751 | 146/152 | 146/152 | 144/144 | 148/152 | 150/154 | 144/154 | 152/152 | 144/152 | 144/144 | 144/144 | 152/154 | 152/154 | 144/152 |
| B741 | 178/184 | 184/184 | 186/188 | 178/184 | 176/184 | 178/186 | 178/186 | 178/186 | 176/186 | 178/188 | 178/186 | 186/186 | 184/186 |
| KG807 | 242/252 | 242/252 | 242/252 | 238/238 | 238/252 | 238/252 | 230/252 | 242/252 | 252/252 | 252/252 | 242/252 | 238/242 | 252/252 |
| B795 | 333/333 | 333/333 | 317/319 | 317/333 | 315/333 | 333/333 | 333/333 | 333/333 | 333/333 | 317/333 | 333/333 | 321/333 | 299/333 |
| B634 | 228/228 | 228/228 | 222/234 | 220/240 | 228/228 | 228/228 | 236/236 | 228/228 | 228/228 | 222/228 | 228/236 | 228/236 | 228/236 |
| B657 | 223/227 | 223/227 | 225/229 | 211/227 | 219/227 | 219/223 | 219/229 | 211/227 | 227/227 | 211/219 | 221/223 | 219/227 | 219/223 |

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

cacacgcctt gtcactcttt                                                20


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

ccccttttcac atgtttgctt                                               20


<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3

tggcagagct ttgtcagctt                                                20


<210> SEQ ID NO 4
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 4 gcagtggagg attgctgact 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5 cactcatacc gcaaactcca 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6 atggcttttg cttcgttttg 20

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7 tgcctctgca gttagtcatc aaatgtagg 29

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8 cgccatataa ttgggatgct tgttg 25

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9 tccgtgttga gtatggacga 20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10 tgtttttggt ggagcgatg 19

<210> SEQ ID NO 11

-continued

<211> LENGTH: 19
<212> TYPE: DNA
<213> ORGANISM: Artificial Sequence
<220> FEATURE:
<223> OTHER INFORMATION: Primer

<400> SEQUENCE: 11 agtcggctcc ccttttctc 19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12 gcgatctgac ctcatttttg 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13 cctgcatcca ggactcatta 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14 gtgcagaggt tgcactcaaa 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15 gagagtgcgt cttcctctgg 20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16 agcctcacct ccaacgaac 19

<210> SEQ ID NO 17
<211> LENGTH: 21
<212> TYPE: DNA
<213> ORGANISM: Artificial Sequence
<220> FEATURE:
<223> OTHER INFORMATION: Primer -continued

<400> SEQUENCE: 17 cgaaagatgg acttccatga c 21

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18 caagttgaga ttcttcctgc aa 22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19 ttgccagtgc atactctgat g 21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 accagctctg ggcttaacac 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 ccaagcacga atgaactcaa 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 gcgggttctc gttgtacact 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23 caccctcttc accacctcat 20

<210> SEQ ID NO 24

-continued

<211> LENGTH: 20
<212> TYPE: DNA
<213> ORGANISM: Artificial Sequence
<220> FEATURE:
<223> OTHER INFORMATION: Primer

<400> SEQUENCE: 24 catcccctgt tggagttttc 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25 gttcacaggc tgttgggttt 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26 cgtgttgctc atgtgttgtg 20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27 ggctgacaac acagcagaaa 20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28 tcggctaggg ttagggtttt 20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29 agctggttct tcgacattcc 20

<210> SEQ ID NO 30
<211> LENGTH: 23
<212> TYPE: DNA
<213> ORGANISM: Artificial Sequence
<220> FEATURE:
<223> OTHER INFORMATION: Primer -continued

<400> SEQUENCE: 30 aaactcaaat aaaacccctg ctc 23

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31 ccaccaactg tttcacacca 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32 gcgaaatgga gctcttgaac 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33 gttttgcgag ctcattgtca 20

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34 tgtgtgtggt ctgtaggcac t 21

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35 gacccacaaa caataaccta tctc 24

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36 tgggcatcat ccaggtcta 19

<210> SEQ ID NO 37

-continued

<211> LENGTH: 22
<212> TYPE: DNA
<213> ORGANISM: Artificial Sequence
<220> FEATURE:
<223> OTHER INFORMATION: Primer

<400> SEQUENCE: 37 cattttccgc agataataca gg 22

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38 gtttccagat ctgcctccat ataat 25

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39 aagcaagaaa gggatggt 18

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40 cttacagata aatggctcaa a 21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41 ggaaggtgag agaaatcaag t 21

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42 aggcatcagt tcatccaa 18

<210> SEQ ID NO 43
<211> LENGTH: 21
<212> TYPE: DNA
<213> ORGANISM: Artificial Sequence
<220> FEATURE:
<223> OTHER INFORMATION: Primer -continued

<400> SEQUENCE: 43 gaacaactga agacagcaaa g 21

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44 aaggcggcac tcgctcac 18

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45 agaactccga ctaataatcc taacccttgc 30

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46 gagggagcaa gtcaaagttg agaagaaa 28

<210> SEQ ID NO 47
<211> LENGTH: 29
<212> TYPE: DNA
<213> ORGANISM: Artificial Sequence
<220> FEATURE:
<223> OTHER INFORMATION: Primer

<400> SEQUENCE: 47 tggaggaagt tttgaatggt agtagagga 29

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48 aaagcaactc atagctgaag tccaatca 28

We claim:

1. A new and distinct cultivar of *Corylus* plant as herein illustrated and described.

* * * * *

FIG. 2

| | | | Jan | | | | | | Feb | | | | | | March | | | |
|---|---|---|---|---|---|---|---|---|---|---|---|---|---|---|---|---|---|---|
| Genotype | 24-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 28-Feb | 7-Mar | 11-Mar | 15-Mar | 27-Mar |
| **Redleaf Cutleaf** | | | | | | | | | | | | | | | | | | |
| 954.076 | | | | | | | | | | 25 | 90 | -90 | | | Gr tip | | no BB as of 3/22 | |
| R150.33 | | | | | | | | | Rd | Rd-2/1 | b3 | b3/1S | | | MS | | | |
| | | | | | | | | | | Red | | | | | Black | | | |
| | | | | | | | | | | | | | | | | | BB | |
| Greenleaf Cutleaf | | | | | | | | | | | | | | 1st | 10 | 25 | 50 | |
| 372.039 | | | | | | | | | | Rd7/1-2/1S | b2/1S | MS | | | MS | | MS | |
| small female flowers | | | | | | | | | | Red | | Bright Red | | | Red | | Dark | |

Bottom (12/2013 - 3/2014)

| | | | Jan | | | | | | Feb | | | | | | March | | | |
|---|---|---|---|---|---|---|---|---|---|---|---|---|---|---|---|---|---|---|
| Genotype | 24-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 28-Feb | 7-Mar | 11-Mar | 15-Mar | 27-Mar |
| **Redleaf Cutleaf** | | | | | | | | | | | | | | | | | | |
| OSU 954.076 | | | | | | | 1st | 80 | | 30-40* | 50-60 | done | | | gr tip | | BB Mar 21 | |
| RL/OL | | | | | | Rd-1st | | | | Rd-3 | Rd-3S | Rd4-3S | b2/Rd-3 | | | | | |
| catkins look good | | | | | | | | | | Red | | Red | dk/blk | | | | | |
| Greenleaf Cutleaf | | | | | | | | | | | 1 | 5 | 20 | | 30 | gr tip | BB Mar 18 | |
| OSU 372.029 | | | | | | | | | | | Rd8 | Rd4-2/S | MS | | | MS | | |
| small females | | | | | | | | | | | Red | Red | Red | | | Red/dark | | |
| **Barcelona** | | | | 1st | 30 | 55 | 90-8 | -70 | | -90 | done | | gr tip | | BB Mar 5 | | | |
| (1.2) | | Rd | Rd-2 | Rd-2/l | | | | b3 | | b3 | | b3 | | | | | | |
| | | | Red | | | | | dk | | dk/red | | black | | | | | | |

S indicate abundance of flowers in each stage

Green = Pollen shed (a minus sign in front of the number indicates the percent of catkins that have already shed out);

Red = Female flowers; red, blk (black), dk (dark, not quite red, not yet black).

'Barcelona' 'Cutleaf' 'Burgundy Lace'